United States Patent [19]

Hunt

[11] 4,415,584

[45] Nov. 15, 1983

[54] 3-OXO-6-OXA-2-AZATRICYCLO 5.4.2. UNADECENE-4-CARBOXYLATE

[75] Inventor: Eric Hunt, Betchworth, England

[73] Assignee: Beecham Group Limited, England

[21] Appl. No.: 6,436

[22] Filed: Jan. 25, 1979

[30] Foreign Application Priority Data

Feb. 2, 1978 [GB] United Kingdom ............... 4152/78

[51] Int. Cl.³ .................. C07D 498/04; A61K 31/42
[52] U.S. Cl. ................................. 424/272; 260/245.3
[58] Field of Search ..................... 260/307 FA, 245.3; 424/272

[56] References Cited

U.S. PATENT DOCUMENTS 4,036,969 7/1977 Stirling ..................... 260/307 FA

OTHER PUBLICATIONS

Merck Index, p. 1005.
Melmon, "Clinical Pharmacology", p. 47.
"Nomenclature of Organic Chemistry", 1979 Edition 1. U.P.A.C., pp. 202, 206.
Naming Organic Compounds, 2nd Edition, Banks, p. 191.
An Introduction to Chemical Nomenclature, 4th Ed., Cahn, p. 98.
Condensed Chemical Dictionary, 9th Edition, p. 16.
Organic Chemistry, vol. 1 (FINAR), p. 222.
"Organic Chemistry, 2nd Edition 1964", Cram et al., pp. 90–91.
Kingzett's Chemical Encyclopedia, 9th Edition, p. 18.

Primary Examiner—Mark L. Berch
Attorney, Agent, or Firm—Jacobs & Jacobs

[57] ABSTRACT

Compounds of the formula (II):

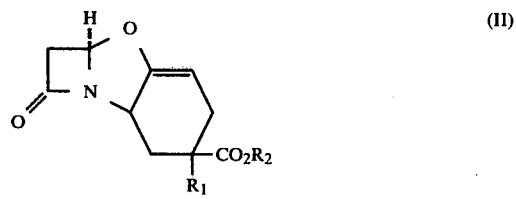

(II)

wherein $R_1$ is hydrogen or alkyl of 1 to 4 carbon atoms, $CO_2R_2$ is a carboxyl group, a pharmaceutically acceptable salt thereof or a pharmaceutically acceptable esterified carboxyl group, are useful for their β-lactamase inhibitory activity and to synergize the antibacterial activity of penicillins and cephalosporin.

66 Claims, No Drawings

3-OXO-6-OXA-2-AZATRICYCLO 5.4.2. UNADECENE-4-CARBOXYLATE

This invention relates to tricyclic β-lactam containing compounds, to a process for their preparation, and to compositions containing them.

European Patent Application No: 78300054.0 (see also U.S. Ser. No: 921738) discloses inter alia the compound of the formula (I):

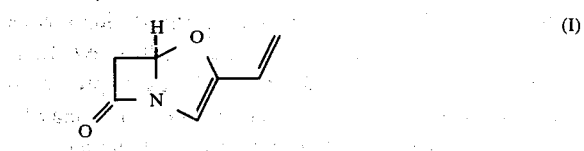

It has now been discovered that a new class of β-lactamase inhibitors may be produced by the reaction of this compound with certain α,β-unsaturated carbonyl compounds.

Accordingly, the present invention provides the compounds of the formula (II):

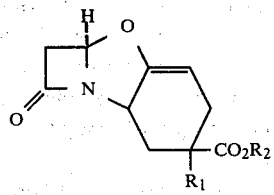

wherein $R_1$ is hydrogen or a $C_{1-4}$ alkyl group and $CO_2R_2$ is a carboxyl group or a salted or esterified carboxyl group.

Preferably, $R_1$ is a hydrogen atom or a methyl group; more preferably, $R_1$ is a hydrogen atom.

Thus, suitable compounds of the formula (II) include those of the formula (III):

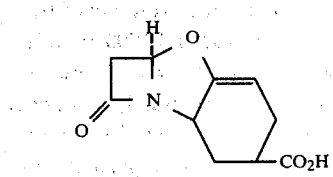

and salts thereof.

Suitable salts of the compound of the formula (III) include alkali and alkaline earth metal salts, and salts with nitrogenous bases such as ammonia or pharmaceutically acceptable amines. Thus suitable salts include lithium, sodium, potassium, calcium, magnesium and ammonium salts.

A further group of suitable compounds of the formula (II) are those of the formula (IV):

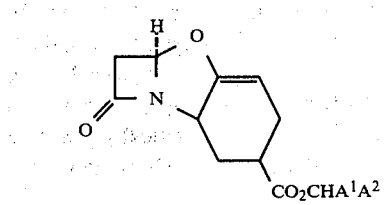

wherein $A^1$ is a hydrogen atom or an alkyl group of 1–4 carbon atoms, an alkenyl or alkynyl group of 2–4 carbon atoms, a phenyl group or a phenyl group substituted by $C_{1-4}$ alkyl, $C_{1-4}$ alkoxy, nitro or halogen; and $A^2$ is a hydrogen atom or an alkyl group 1–4 carbon atoms, an alkoxy group of 1–4 carbon atoms, an acyloxy group of 1–5 carbon atoms, a phenyl group, or a phenyl group substituted by $C_{1-4}$ alkyl, $C_{1-4}$ alkoxy, nitro or halogen.

A further group of suitable esters are those of the formula (V):

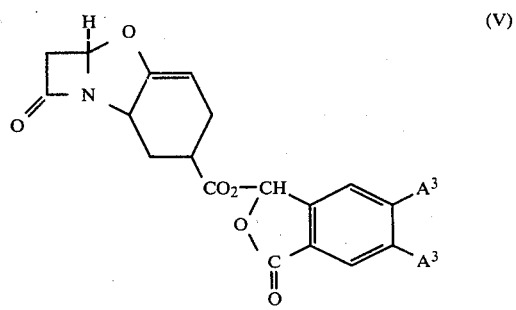

wherein $A^3$ is a hydrogen atom or a methyl or methoxyl group.

Favoured esters of the formulae (IV) and (V) are methyl, ethyl, benzyl, p-methoxybenzyl, p-nitrobenzyl, methoxymethyl, acetoxymethyl, pivaloyloxmethyl, phthalidyl and the like esters.

The compounds of the formulae (III), (IV) and (V) may have either R or S stereochemistry at C-1 and at C-10.

The atom numbering scheme used herein is shown on the skeleton below:

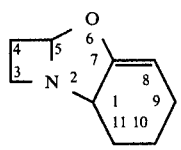

This invention also provides a process for the preparation of a compound of the formula (II), which process comprises the reaction of the compound of the formula (I) with a compound of the formula (VI):

$$CH_2=CR_1CO_2R_3 \qquad (VI)$$

wherein $R_1$ is as defined in relation to formula (II) and $CO_2R_3$ is an esterified carboxyl group, and thereafter, if desired, converting the thus-produced ester of the formula (II) to the free acid or a salt or alternative ester thereof.

The addition of the compounds of the formulae (I) and (VI) is generally carried out at an elevated temperature such as 60°–100° C., for example 70°–90° C.

If the ester of the formula (VI) is liquid at room temperature, it may act as solvent for the reaction. Under these conditions, it will usually be used in a large excess. Suitable inert solvents may also be employed, such as benzene, toluene, tetrahydrofuran, 1,2-dimethoxyethene, or the like.

Once the reaction is complete, for example as judged by tlc using silica gel with ethyl acetate/petroleum ether as solvent, the solvent may be removed by evaporation and the residue purified if desired by chromatography, for example on silica gel using ethyl acetate/petroleum ether, hplc or the like. Fractions for collection may be identified by tlc, using Ehrlich's reagent to visualise the product.

In this procedure, the isomers of the compound of the formula (II) may be separated from each other and from the corresponding 11-substituted compounds produced in the addition reaction.

In a further process aspect of this invention, compounds of the formula (II) wherein $CO_2R_2$ is a carboxyl or salted carboxyl group may be prepared by the oxidation of the corresponding aldehydes of the formula (VII):

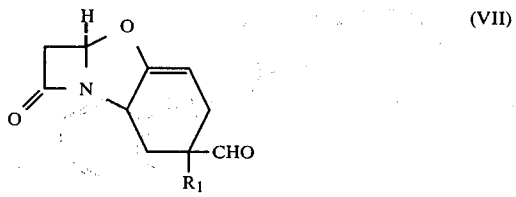

wherein $R_1$ is as defined in relation to formula (II). Such reactions may be carried out by mild oxidising agents, such as silver oxide, or oxygen in the presence of a transition metal catalyst, for example, platinum.

The compounds of the formula (VII) are useful intermediates in the preparation of compounds of the formula (II), and, as such, form an aspect of this invention.

The compounds of the formula (VII) may be prepared by the reaction of a compound of the formula (VIII):

$$CH_2=CR_1CHO \qquad (VIII)$$

wherein $R_1$ is as defined in relation to formula (II) with the compound of the formula (I).

The reaction conditions in this process will be similar to those described for the reaction of the compounds of the formulae (I) and (VI).

Compounds of the formula (II) wherein $CO_2R_2$ represents a free carboxyl group may also be prepared by the hydrogenolysis of a corresponding hydrogenolysable ester.

Normally the hydrogenolysis will be carried out in an inert solvent, such as tetrahydrofuran, in the presence of a transition metal catalyst, for example, palladium on charcoal.

Suitable hydrogenolysable esters include the benzyl and substituted benzyl esters.

If a base is present during the hydrogenolysis reaction, then the product will be obtained in the form of a salt.

The C-10 isomers of the compounds of the formula (II) may be interconverted by treatment with a base such as lithium bis-(trimethylsilyl)-amide in an inert solvent under anhydrous conditions at a depressed temperature.

In a further aspect, this invention provides a pharmaceutical composition comprising a compound of the formula (II) and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Unit dose compositions comprising a compound of the formula (II) adapted for oral administration form a further preferred composition aspect of this invention.

The compound of the formula (II) may be present in the composition as sole therapeutic agent or it may be present together with other therapeutic agents such as a $\beta$-lactam antibiotic, for example, a penicillin or cephalosporin.

Naturally if the penicillin or cephalosporin present in the composition is not suitable for oral administration then the composition will be adapted for parenteral administration.

When present in a pharmaceutical composition together with a $\beta$-lactam antibiotic, the weight ratio of the compound of the formula (II) present to $\beta$-lactam antibiotic present may vary over a wide range, for example 10:1 to 1:3 and advantageously may be from 5:1 to 1:2, for example, 3:1 to 1:1.

The total quantity of antibacterial agents present in any unit dosage form will normally be between 50 and 1500 mg and will usually be between 100 and 1000 mg.

Compositions of this invention may be used for the treatment of infections of inter alia, the respiratory tract, the urinary tract and soft tissues, and mastitis in cattle.

Normally between 50 and 3000 mg of the compounds of the invention will be administered each day of treatment but more usually between 100 and 1000 mg of the compounds of the invention will be administered per day, for example as 1-6 doses, more usually 2-4 doses.

The penicillin or cephalosporin in synergistic compositions of this invention will normally be present by up to or at approximately the amount at which it is conventionally used.

Particularly favoured compositions of this invention will contain from 150-1000 mg of amoxycillin, ampicillin or a pro-drug therefor and from 50-500 mg of a compound of the formula (II) and more suitably from 200-500 mg of amoxycillin, ampicillin or a pro-drug therefor and from 50-250 mg of a compound of the formula (II).

The materials present in such compositions may be hydrated if required, for example, ampicillin trihydrate or amoxycillin trihydrate may be employed. The weights of the antibiotics in such compositions are expressed on the basis of antibiotic theoretically available from the composition and not on the basis of the weight of pro-drug.

The following Examples illustrate the invention.

EXAMPLE 1

(5R)-10-Methoxycarbonyl-3-oxo-6-oxa-1-azatricyclo[5.4.0.0^{2,5}]-undec-7,8-ene.

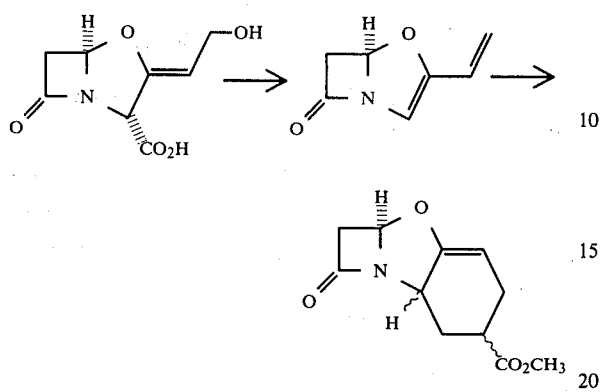

Clavulanic acid (3.0 mmole) in dry tetrahydrofuran (10 ml) and N,N-dimethylformamide dimethylacetal (0.4 g., 3.35 mmole) in dry tetrahydrofuran (10 ml) were added simultaneously to a rapidly stirred solution of hydroquinone (20 mg) in tetrahydrofuran (20 ml) at room temperature. After addition was complete (5 minutes), the mixture was decolourised using charcoal and filtered, the filter being washed well with more tetrahydrofuran. The solvent was evaporated from the filtrate under reduced pressure to yield (5R)-3-vinyl-7-oxo-4-oxa-1-azabicyclo[3.2.0]-hept-2-ene (340 mg., 2.5 mmole) as a colourless oil, which was immediately dissolved in methyl acrylate (15 ml). The resulting solution was heated at 80° (bath temperature) for 2 hours, then the methyl acrylate was evaporated under reduced pressure and the resulting residue was chromatographed on silica gel using ethyl acetate/protroleum ether (b.p. 60°–80°). Isomer I of the title compound was thus obtained as a colourless gum (84 mg), $[\alpha]_D^{25} = +308.5°$ (c 1.0, CHCl$_3$). (Found: M$^+$, 223.0839; C$_{11}$H$_{13}$NO$_4$ requires 223.0844). $\nu_{max}$ (CHCl$_3$): 1795 ($\beta$-lactam C=O), 1735 (ester C=O), 1710 (sh)(C=C) cm$^{-1}$. $\delta$(CDCl$_3$): 1.56 (1, J 12 Hz, 1H, C(11)H), 2.0–2.8 (complex, 4H), 2.93 (d, J 16 Hz, 1H C(4)H), 3.29 (dd, J 16, 2 Hz, 1H, C(4)H), 3.65 (s, 3H, CO$_2$CH$_3$), 4.10 (ddd, J 12, 4, 2 Hz, 1H C(1)H), 5.11 (m, 2H, C(5)H and C(8)H). m/e: 223 (M$^+$, 20%), 195 (33), 192(25), 182(3), 167(10), 164(17), 154(40), 122(30), 121(15), 95(100), 94(24). Isomer II of the title compound was also obtained as a colourless gum (45 mg), $[\alpha]_D^{25} = +181.9°$ (c 1.0, CHCl$_3$). Found: M, 223.0849; C$_{11}$H$_{13}$NO$_4$ requires 223.0844). $\nu_{max}$ (CHCl$_3$): 1792 ($\beta$-lactam C=O), 1735 (ester C=O), 1710 (sh)(C=C) cm$^{-1}$. $\delta$(CDCl$_3$): 1.55 (dt, J 6, 12 Hz, 1H C(11)H), 2.0–3.0 (complex, 4H) 2.92 (d, J 16 Hz, 1H, C(4)H), 3.28 (dd, J 16, 2 Hz, 1H C(4)H), 3.69 (s, 3H, CO$_2$CH$_3$), 4.05 (ddd, J 12, 5, 2 Hz, 1H, C(1)H), 5.10 (m, 2H, C(5)H, C(8)H). m/e: 223 (M$^+$, 6%), 195(22), 192(17), 182(14), 167(8), 164(10), 154(3), 122(37), 121(95), 95(52), 94(20), 55(100).

The two products described above could also be separated using h.l.p.c. For example, using a 20 cm×1 cm. column of 5$\mu$ "Lichrasorb" and 1:3 ethyl acetate/cyclohexane as solvent with a flow rate of 3 ml/min., Isomer I of the title compound had a retention time of 7.6 mins. and Isomer II had a retention time of 8.35 mins.

EXAMPLE 2

(5R)-10-Benzyloxycarbonyl-3-oxo-6-oxa-2-azabicyclo[5.4.0.0^{2,5}]-undec-7,8-ene

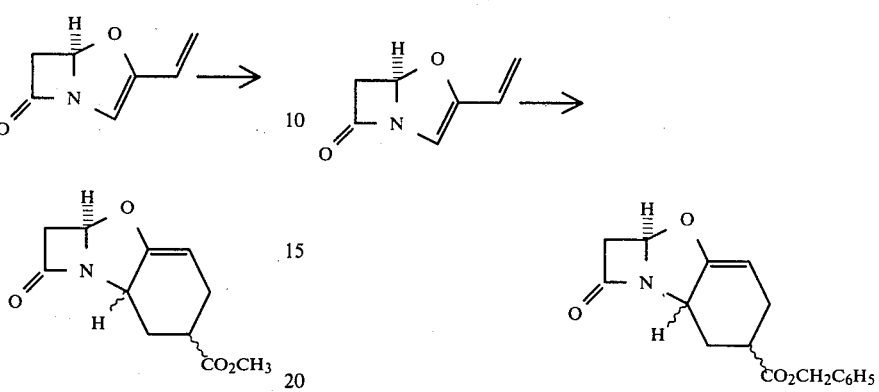

(5R)-3-Vinyl-7-oxo-4-oxa-1-azabicyclo[3.2.0]hept-2-ene (345 mg., 2.5 mmole) was prepared from clavulanic acid (3.0 mmole) as described in Example 1. This diene was dissolved in benzyl acrylate (7 ml) and the resulting solution was heated at 80° (bath temperature) for 1.5 hours. The bulk of the benzyl acrylate was then removed by distillation at 100° (bath temperature)/0.5 mm Hg pressure; and the resulting residue was chromatography on silica gel (25 g) using 1:9→1:4 ethyl acetate/petroleum ether (b,p. 60°–80°) to give, in order of elution, the following compounds: (5R)-11-benzyloxycarbonyl-3-oxo-6-oxa-2-azatricyclo[5.4.0.0^{2,5}]-undec-7,8-ene as colourless prisms (20 mg), isomer I of the title compound as a colourless gum (80 mg), and isomer II of the title compounds as a colourless gum (55 mg).

Isomer I of the title compound had $[\alpha]_D^{22} = +239.1°$ (C 1.0, CHCl$_3$). $\delta_{max}$ (CHCl$_3$): 1780 ($\beta$-lactam C=O), 1730 (ester C=O), 1710 (sh)(olefinic C=C) cm$^{-1}$. $\delta$(CDCl$_3$): 1.56 (q, J 11.5 Hz, 1H, C(11)H), 2.1–3.0 (complex, 5H, C(4)H, C(9)H$_2$, C(10)H), 3.24 (dd, J 15, 2 Hz, C(4)H), 4.09 (ddd, J 11.5, 5.2 Hz, 1 HC(1)H), 5.08 (s overlapping m, 4H, CO$_2$CH$_2$, C(5)H, C(8)H), 7.27 (s, 5H, C$_6$H$_5$). m/e: 208 (C$_{10}$H$_{10}$NO$_4$, 23%), 166 (6), 139 (13), 91 (C$_7$H$_7$, 100). $\nu_{max}$(CHCl$_3$). Isomer II of the title compound had $[\alpha]_D^{22} = +172.2°$ (c, 1.0, CHCl$_3$) 1785 ($\beta$-lactam C=O), 1725 (ester C=O), 1705 (sh)(olefinic C=C) cm$^{-1}$. $\delta$(CDCl$_3$): 1.55 (dt, J 6, 11.5 Hz, 1H, C(11)H), 2.0–3.0 (complex, 5H, C(4)H, C(9)H$_2$, C(10)H), C(11)H), 3.23 (dd, J 16, 2 Hz, 1H, C(4)H), 4.08 (ddd, J 11.5, 5, 2 Hz, 1H, C(1)H), 5.10 (s overlapping m, 4H, CO$_2$CH$_2$, C(5)H, C(8)H), 7.28 (s, 5H, C$_6$H$_5$). m/e: 257 (C$_{15}$H$_{15}$NO$_3$, 7%) 208 (14), 166 (12), 139 (5), 120(8), 91(C$_7$H$_7$, 100).

The two isomers of the title compound could also be separated using h.p.l.c., using a 20 cm×1 cm column of 5$\mu$ "Lichrasorb" with 1:3 ethyl acetate/cyclohexane as solvent and a flow rate of 3 ml/min., Isomer I had a retention time of 5.2 mins. and
Isomer II had a retention time of 6.0 mins.

EXAMPLE 3

Sodium (1S, 5R)-$\Delta^{7,8}$-3-oxo-6-oxa-2-azatricyclo-[5.4.0.0$^{2,5}$]undec-ene-10-carboxylate.

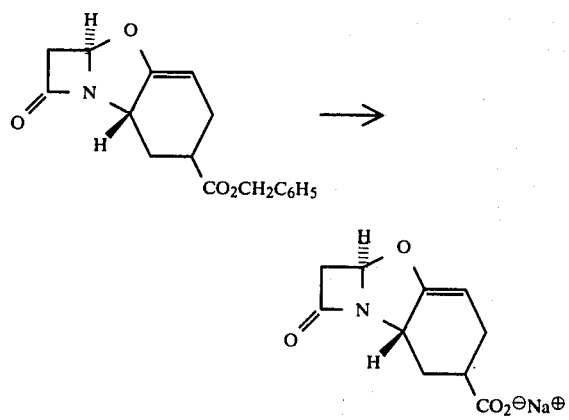

(1S, 5R)-10-Benzyloxycarbonyl-3-oxo-6-oxa-2-azatricyclo[5.2.0.0$^{2,5}$]undec-7,ene (Isomer I from Example 2) (48 mg) was dissolved in tetrahydrofuran (10 ml) and the solution was shaken with 5% palladium-on-charcoal (30 mg) under one atmosphere of hydrogen at room temperature for 4 hours. The catalyst was removed by filtration and was washed well with tetrahydrofuran. 0.1 N Sodium bicarbonate solution (1.6 ml) was added to the filtrate together with water (10 ml) and the tetrahydrofuran was evaporated under reduced pressure. The aqueous residue was washed once with ether (10 ml) and was then freeze-dried to yield the title compound as a pale yellow amorphous powder (23 mg). The product thus obtained appeared to be homogeneous as judged by t.l.c. (50:50:7 chloroform, acetone, acetic acid). $\delta_{max}$ (KBr): 1772 ($\beta$-lactam C=O), 1695 (olefinic C=C), 1560 and 1400 (carboxylate) cm$^{-1}$.

EXAMPLE 4

Antibacterial Synergy

| Compound from Example number | Inhibitor conc. (μg/ml) | MIC for ampicillin (μg/ml) | | | |
|---|---|---|---|---|---|
| | | Staph. aureus Russell | Kleb. aerogenes E70 | P. mirabilis C889 | E. coli JT39 |
| — | — | >500 | 2000 | 2000 | 500 |
| 1 (Isomer II) | 20 | 0.2 | 3.1 | 8–16 | |
| 2 (Isomer II) | 20 | 0.2 | 50 | 16 | 8 |
| 3 | 20 | 0.4 | 3.1 | 1* | ≦0.5 |
| | 5 | 1.6 | 12.5 | 2* | 4 |

*Trailing end-point

Antibacterial Activity

| Compound from Example number | M.I.C. (μg/ml) | | | |
|---|---|---|---|---|
| | Staph. aureus Russell | Kleb. areogenes E70 | P. mirabilis C889 | E. coli JT39 |
| 1 (Isomer II) | 125 | >500 | >500 | |
| 2 (Isomer II) | 62.5 | >500 | >500 | >500 |
| 3 | 125 | >500 | >500 | 250 |

EXAMPLE 5

(5R)-10-Methoxycarbonyl-10-methyl-3-oxo-6-oxa-2-azatricyclo[5.4.0.0$^{2,5}$]undec-7,8-ene

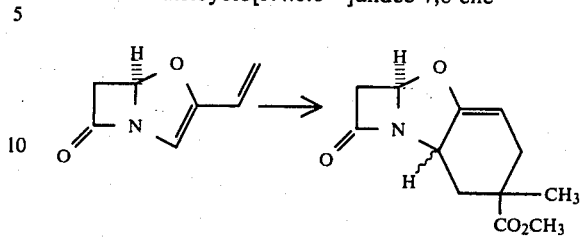

Using the process described in Example 1, (5R)-3-vinyl-7-oxo-4-oxa-1-azabicyclo[3.2.0]hept-2-ene (330 mg) was brought into reaction with methyl methacrylate (15 ml). After chromatography on silica gel, isomer I of the title compound was obtained as a colourless gum (22 mg) and isomer II of the title compound was also obtained as a colourless gum (19 mg).

Isomer I had $[\alpha]_D^{25} = +260.2°$ (c=1.0, CHCl$_3$), (Found: M$^+$, 237.1002; C$_{12}$H$_{15}$NO$_4$ requires 237.1001). $\nu_{max}$ (CHCl$_3$): 1790 ($\beta$-lactam C=O), 1730 (ester C=O), 1700 (sh)(olefinic C=C) cm$^{-1}$ m/e: 237 (M$^+$, 3%), 209 (10), 195 (17), 178 (13), 136 (62), 135 (46), 109 (70), 108 (27), 95 (100).

Isomer II had $[\alpha]_D^{25} = +148.3°$ (c=0.95, CHCl$_3$). $\nu_{max}$ (CHCl$_3$): 1790 ($\beta$-lactam C=O), 1730 (ester C=O), 1700 (sh) (olefinic C=C) cm$^{-1}$ m/e: 165 (C$_9$H$_{11}$NO$_2$, 10%), 131 (24), 119(50), 94(100).

EXAMPLE 6.1

(1S, 5R, 10S)-10-Formyl-3-oxo-6-oxa-2-azatricyclo[5.4.00.$^{2,5}$]-undec-7,8-ene

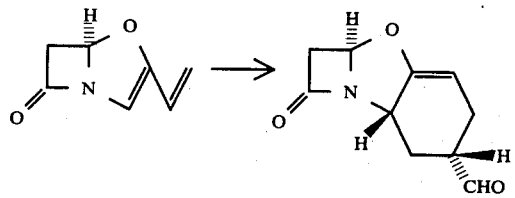

(5R)-3-Vinyl-7-oxo-4-oxa-1-azabicyclo[3.2.0]hept-2-ene (340 mg) was dissolved in acrolein (15 ml) together with hydroquinoline (100 mg). The resulting mixture was heated at 50° C. under a dry nitrogen atmosphere for 3.5 hours. The acrolein was then evaporated under reduced pressure and the residue was chromatographed on silica gel using ethyl acetate/petroleum ether (b.p. 60°–80°). The title compound was thus obtained as colourless crystals (97 mg). Recrystallisation from ethyl acetate/petroleum ether (b.p. 60°–80°) gave colourless prisms, m.p. 94°–95° (Found: C, 61.89; H, 5.89; N, 6.99. C$_{10}$H$_{11}$NO$_3$ requires C, 62.17; H, 5.74; N, 7.25%). $\nu_{max}$ (CHCl$_3$): 2800 (aldehyde C-H), 1785 ($\beta$-lactam C=O), 1720 (aldehyde C=O), 1700 (sh) (olefinic C=C) cm$^{-1}$. $\delta$ (CDCl$_3$): 1.39 (q, J 12 Hz, 1H, C(11)H), 2.2–2.8 (complex, 4H, C(9)H$_2$, C(10)H), 2.95 (d, J 16 Hz, 1H C(4)H), 3.32 (dd, J 16, 2.5 Hz, 1H, C(4)H), 4.18 (ddd, J 12, 4, 2 Hz, 1H, C(8)H), 5.15 (m, 2H, C(1)H, C(5)H), 9.60 (s, 1H, aldehyde-H). m/e: 193 (M$^+$, C$_{10}$H$_{11}$NO$_3$, 0.5%), 151 (0.5), 122 (2), 120 (1), 119 (12), 99(27), 95(55), 67(42), 55(100).

EXAMPLE 6.2

Sodium (1S, 5R, 10S)-7,8-3-oxo-6-oxa-2-azatricyclo-[5.4.0.0^{2,5}]undecene-10-carboxylate

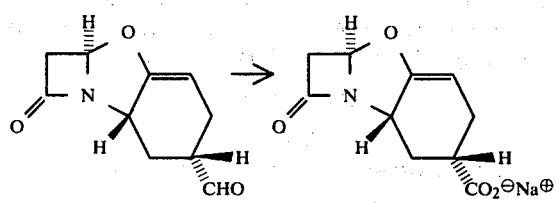

(1S, 5R, 10S)-10-Formyl-3-oxo-6-oxa-2-azatricyclo[5.4.0.0.$^{2,5}$]undec-7,8-ene (90 mg) and sodium bicarbonate (40 mg) were dissolved in a mixture of tetrahydrofuran (6 ml) and water (3 ml). 5% Platinium-on-charcoal (90 mg) was added to the solution which was then stirred while oxygen was bubbled through at 50° for 2 hours and then at 23° for 16 hours. The catalyst was removed by filtration and was washed well with water. The tetrahydrofuran was evaporated from the combined filtrate and washings and the resulting aqueous residue was washed once with ether. The aqueous solution was then freeze-dried to give the title compound as a pale brown amorphous powder (75 mg). $v_{max}$ (KBr): 1772 ($\beta$-lactam C=O), 1695 (olefinic C=C), 1560 and 1400 (carboxylate) cm$^{-1}$.

EXAMPLE 6.3

(1S, 5R, 10S)-10-Benzyloxycarbonyl-3-oxo-6-oxa-2-azatricyclo[5.4.0.0$^{2,5}$]undec-7,8-ene

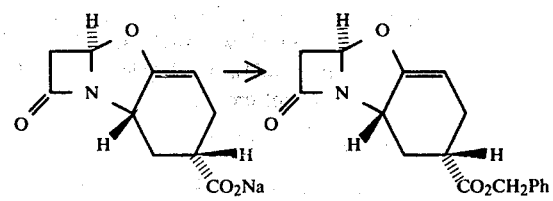

Sodium (1S, 5R, 10S)-$\Delta^{7,8}$-3-oxo-6-oxa-2-azatricyclo[5.4.0.0$^{2,5}$]undecene-10-carboxylate (20 mg) was dissolved in dry hexamethylphosphoramide (3 ml) and benzyl bromide (30 mg) was added to the solution. The mixture was stirred at room temperature with exclusion of moisture for 18 hours and was then diluted with ethyl acetate (50 ml) and was washed three times with water (20 ml portions). The solution was dried (sodium sulphate) and the solvent was evaporated under reduced pressure to yield a dark coloured gum. The gum was chromatographed on silica gel using ethyl acetate/petroleum ether (b.p. 60°-80°) to give the title compound as a pale yellow gum (9 mg), $[\alpha]_D^{22} = +237°$ (c 0.9, CHCl$_3$). The product thus obtained has spectoscopic and chromatographic properties identical to those for isomer I from Example 2.

EXAMPLE 7

(1S, 5R, 10R)-10-Benzyloxycarbonyl-3-oxo-6-oxa-2-azatricyclo[5.4.0.0$^{2,5}$]undec-7,8-ene

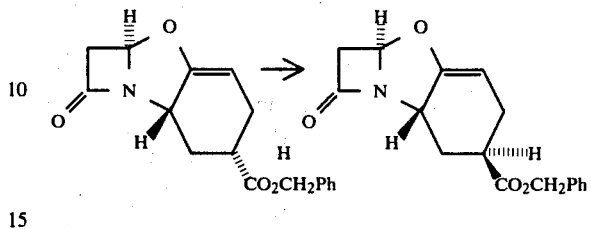

(1S, 5R, 10S)-10-Benzyloxycarbonyl-3-oxo-6-oxa-2-azatricyclo[5.4.0.0$^{2,5}$]undec-7,8-ene, isomer I from Example 2, (75 mg, 0.25 mmole) in dry tetrahydrofuran (1 ml) was added dropwise to a stirred solution of lithium bis(trimethylsilyl)amide (0.5 mmole) in tetrahydrofuran (10 ml) at −70° under dry nitrogen. 20 minutes after addition was complete, the mixture was poured into water (100 ml) and was extracted twice with ethyl acetate (50 ml portions). The combined organic extracts were dried (sodium sulphate) and the solvent was evaporated under pressure to yield a yellow gum. The gum was chromatographed on silica gel using ethyl acetate/petroleum ether (b.p. 60°-80°) to give, in order of elution, the starting compound (5 mg) and the title compound (10 mg), both as colourless gums. The title compound had the following spectroscopic properties. $v_{max}$ (CHCl$_3$): 1780 ($\beta$-lactam C=O), 1730 (ester C=O), 1705 (olefinic C=C) cm$^{-1}$. $\delta$ (CDCl$_3$): 1.6–2.8 (complex, 5H, C(9)H$_2$, C(11)H$_2$), 2.85 (d, J 16 Hz, 1H, C(4)H), 3.63 (m, 1H, C(1)H), 4.88 (m, 1H, C(8)H), 5.09 (s, 2H, OCH$_2$Ph), 5.37 (d, J 2 Hz, C(5)H), 7.27 (s, 5H, C$_6$H$_5$).

EXAMPLE 8

(5R)-10-Pivaloyloxymethoxycarbonyl-3-oxo-6-oxa-2-azatricyclo[5.4.0.0$^{2,5}$]undec-7,8-ene

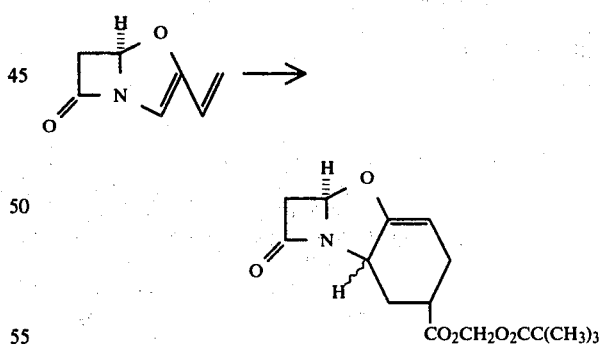

(5R)-3-Vinyl-7-oxo-4-oxa-1-azabicyclo[3.2.0]hept-2-ene (330 mg., 2.4 mmole) and pivaloyloxymethyl acrylate (8.5 g.) were converted into the title compounds using the process described in Example 2. In order of elution, the following compounds were obtained from the chromatography (5R)-11-pivaloyloxymethoxycarbonyl-3-oxo-6-oxa-2-azatricyclo[5.4.0.0$^{2,5}$]undec-7,8-ene as a colourless gum (15 mg), isomer I of the title compound, (1S, 5R, 10S)-10-pivaloyloxymethoxycarbonyl-3-oxo-6-oxa-2-azatricyclo[5.4.0.0$^{2,5}$]undec-7,8-ene, as a colourless gum (145 mg), and isomer II of the title compound as a colourless gum (80 mg).

Isomer I had $[\alpha]_D^{21} = +227.7°$ (c 1.0, CHCl$_3$). (Found: M$^+$, 323.1293; C$_{16}$H$_{21}$NO$_6$ requires 323.1369). $\nu_{max}$ (CHCl$_3$): 1790 ($\beta$-lactam C=O), 1750 (ester C=O), 1705 (olefinic C=C) cm$^{-1}$. $\delta$ (CDCl$_3$): 1.20 (s, 9H, C(CH$_3$)$_3$), 1.56 (q, J 11 Hz, 1H, C(11)H), 2.0–2.8 (complex, 4H, C(9)H$_2$, C(10)H, C(11)H), 2.91 (d, J 16 Hz, 1H, C(4)H), 3.28 (dd, J 16, 2 Hz, 1H, C(4)H), 4.10 (ddd, J 11, 4, 2 Hz, 1H, C(1)H), 5.10 (m, 2H, C(5)H, C(8)H), 5.70 (s, 2H, OCH$_2$O). m/e: 323 (M$^+$, 0.2%), 192(26), 191(18), 57(100).

Isomer II has $[\alpha]_D^{21} = +139.5°$ (c 1.0, CHCl$_3$). (Found: M$^+$, 323.1369; C$_{16}$H$_{21}$NO$_6$ requires 323.1369). $\nu_{max}$ (CHCl$_3$): 1785 ($\beta$-lactam C=O), 1750 (ester C=O), 1705 (olefinic C=C) cm$^{-1}$. $\delta$ (CDCl$_3$): 1.20 (s, 9H, C(CH$_3$)$_3$), 1.57 (dt, J 6, 12 Hz, 1H, C(11)H), 2.1–3.0 (complex, 4H, C(9)H$_2$, C(10)H, C(11)H), 2.93 (d, J 16 Hz, 1H, C(4)H), 3.29 (dd, J 16, 2 Hz, 1H, C(4)H), 4.08 (ddd, J 12, 4, 2 Hz, 1H C(1)H), 5.12 (m, 2H, C(5)H), C(8)H, 5.71 (s, 2H, OCH$_2$O). m/e: 323 (M$^+$0.1%), 208(9), 85(30), 57(100).

EXAMPLE 9

(5R)-10-p-Nitrobenzyloxycarbonyl-3-oxo-6-oxa-2-azatricyclo[5.4.0.0$^{2,5}$]undec-7,8-ene

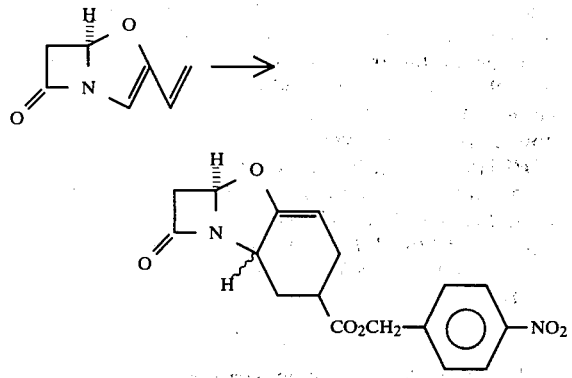

(5R)-3-Vinyl-7-oxo-4-oxa-1-azabicyclo[3.2.0]hept-2-ene (4 mmole); prepared from 1.01 g clavulanic acid according to Example 1) was dissolved in dry 1,2-dimethyxyethane (10 ml) containing hydroquinolinone (50 mg). p-Nitrobenzyl acrylate (1.8 g) was added to the solution which was then heated at 85° (bath temperature) with exclusion of moisture for 2.5 hours. The mixture was cooled, diluted with ethyl acetate (50 ml), and filtered. The solvent was evaporated from the filtrate under reduced pressure to give a yellow oil which was chromatographed on silica gel (15 g) using gradient elution from 1:7 to 1:3 ethyl acetate/petroleum ether (b.p. 60°–80°). In this way the title compound (Mixture of isomers) was obtained as a yellow gum (150 mg).

The above experiment was repeated (starting with 1.1 g clavulanic acid) to give a further quantity (100 mg) of the mixed isomers of the title compound.

The mixed isomers of the title compound (250 mg) were chromatographed on silica gel (20 g) using gradient elution from 1:6 to 1:3 ethyl acetate/petroleum ether (b.p. 60°–80°) to give, in order of elution, isomer I of the title compound, (1S, 5R, 10S)-10-p-nitrobenzyloxycarbonyl-3-oxo-6-oxa-2-azatricyclo[5.4.0.0$^{2,5}$]undec-7,8-ene, as a colourless gum (130 mg) and isomer II of the title compound as a colourless gum (70 mg).

Isomer I had $[\alpha]_D^{20} = +175.2°$ (c 1.0, CHCl$_3$). $\nu_{max}$ (CHCl$_3$): 1785, 1735, 1705, 1605, 1520, 1350 cm$^{-1}$. $\delta$ (CDCl$_3$): 1.60 (1H, q, J 12 Hz), 2.0–3.1 (5H, complex), 3.32 (1H, dd, J 17 and 2 Hz), 4.15 (1H, ddd, J 12, 5 and 2 Hz), 5.23 (4H, s overlapping m), 7.50 (2H, d, J 9 Hz), 8.23 (2H, d, J 9 Hz).

Isomer II had $[\alpha]_D^{20} = +143.5°$ (c 1.0, CHCl$_3$). $\nu_{max}$ (CDCl$_3$): 1783, 1735, 1702, 1605, 1520, 1355 cm$^{-1}$. $\delta$ (CDCl$_3$): 1.62 (1H, dt, J 6 and 12 Hz), 2.1–3.1 (5H, complex), 3.30 (1H, dd, J 16 and 2 Hz), 4.05 (1H, ddd, J 12, 5 and 2 Hz), 5.24 (4H, s overlapping m), 7.52 (2H, d, J 9 Hz), 8.23 (2H, d, J 9 Hz).

EXAMPLE 10

Sodium (5R)-$\Delta^{7,8}$-3-oxo-6-oxa-2-azatricyclo[5.4.0.0$^{2,5}$]undec-ene-10-carboxylate

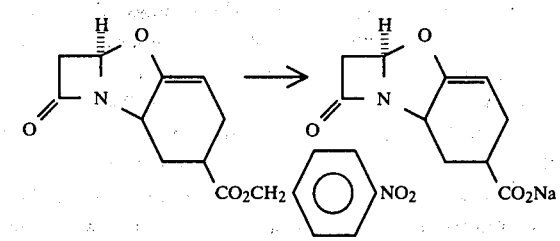

(5R)-10-p-Nitrobenzyloxycarbonyl-3-oxo-6-oxa-2-aztricyclo[5.4.0.0$^{2,5}$]undec-7,8-ene (Isomer II from Example 9; 60 mg) was dissolved in tetrahydrofuran (10 ml) and the solution was shaken with 5% palladium-on-charcoal (40 mg) under 1 atmosphere of hydrogen at room temperature for 1 hour. More catalyst (25 mg) was added and hydrogenation was continued for a further 1 hour. The catalyst was removed by filtration and was washed with tetrahydrofuran (20 ml). Water (10 ml) was added to the filtrate, followed by sodium bicarbonate (0.175 mmole) in water (1 ml). The tetrahydrofuran was evaporated under reduced pressure and the aqueous residue was washed with ether (2×5 ml) and filtered through Celite. The filtrate was freeze-dried to give the title salt as a pale yellow powder (35 mg). $\nu_{max}$ (KBr): 1775 ($\beta$-lactam C=O), 1700 (olefinic C=C), 1565 and 1400 (carboxylate) cm$^{-1}$.

EXAMPLE 11

Sodium (1S, 5R, 10S)-$\Delta^{7,8}$-3-oxo-6-oxa-2-azatricyclo[5.4.0.0$^{2,5}$]undec-ene-10-carboxylate

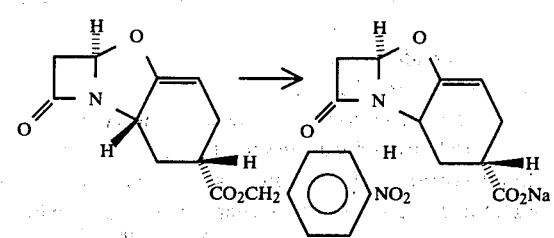

The p-nitrobenzyl ester (Isomer I from Example 9; 125 mg) was converted into the title salt using the process described in Example 10. The title salt was obtained as a pale yellow powder (78 mg). $\nu_{max}$ (KBr): 1780 ($\beta$-lactam C=O), 1700 (olefinic C=C), 1570 and 1405 (carboxylate) cm$^{-1}$.

EXAMPLE 12

In vivo Synergy

Groups of mice were infected intraperitoneally with *E. coli* E96 ($R_{TEM}$), and were then dosed at 1 and 5 hours after infection with amoxycillin or amoxycillin and the compound of Example 3. The $CD_{50}$ values are shown below:

|  | $CD_{50}$ (mg/kg) |
|---|---|
| Amoxycillin alone | 1000 × 2 |
| Amoxycillin + synergist (5 mg/kg) | 140 × 2 |
| Amoxycillin + synergist (10 mg/kg) | 58 × 2 |

Toxicity

The compound of Example 1 (Isomer II) was administered intraperitoneally to mice. After 10 days, no deaths were observed at dosages up to 750 mg/kg.

EXAMPLE 13

Antibacterial Synergy

The MIC's of ampicillin, the product of Example 10 (synergist) and ampicillin in the presence of the product of Example 10 were determined for a range of bacteria. The results are shown below:

| | MIC Ampicillin (μg/ml) | | | |
|---|---|---|---|---|
| Concentration of synergist (μg/ml) | *Staph. aureus* Russell | *Klebsiella aerogenes* E70 | *Proteus mirabilis* C889 | *E. coli* JT39 |
| 20 | 0.08 | inhibition | inhibition | inhibition |
| 5 | 0.16 | 0.8 | 4 | 8 |
| 1 | 0.3 | 3.1 | 62.5* | 62.5 |
| 0 | 500 | 500 | >2000 | >2000 |
| MIC (μg/ml) synergist alone | 125 | 31.2 | 31.2 | 16 |

What we claim is:

1. A compound of the formula (II):

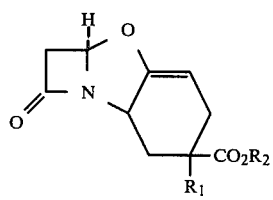

wherein $R_1$ is hydrogen or alkyl of 1 to 4 carbon atoms and $CO_2R_2$ is carboxyl or a pharmaceutically acceptable salt thereof.

2. A compound according to claim 1 wherein $R_1$ is hydrogen or methyl.

3. A compound according to claim 2 of the formula (III):

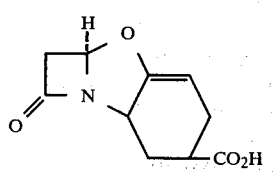

or a pharmaceutically acceptable salt thereof.

4. A compound according to claim 1 in the form of an alkali or alkaline earth metal salt or ammonium salt.

5. A salt according to claim 4 which is, sodium, potassium, calcium, magnesium or ammonium salt.

6. A compound of the formula (IV):

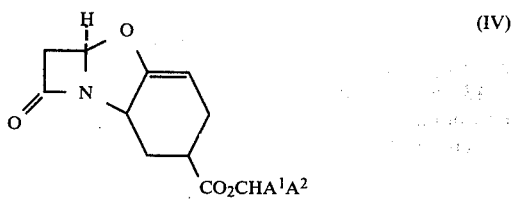

wherein $A^1$ is hydrogen, alkyl of 1 to 4 carbon atoms, alkenyl or alkynyl of 2 to 4 carbon atoms, phenyl, or phenyl substituted by alkyl of 1 to 4 carbon atoms, alkoxy of 1 to 4 carbon atoms, nitro or halogen; and $A^2$ is hydrogen, alkyl of 1 to 4 carbon atoms, alkoxy of 1 to 4 carbon atoms, alkanoyloxy of 1 to 5 cabon atoms, phenyl, or phenyl substituted by alkyl of 1 to 4 carbon atoms, alkoxy of 1 to 4 carbon atoms, nitro or halogen.

7. A compound of the formula (V):

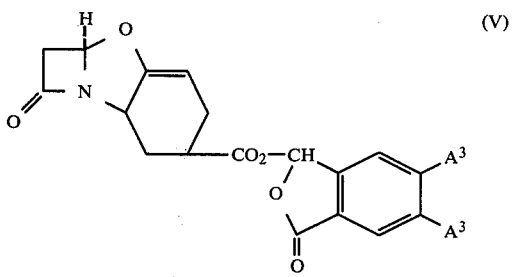

wherein $A^3$ is hydrogen, methyl or methoxy.

8. A compound according to claim 6 which is a methyl, ethyl, benzyl, p-methoxybenzyl, p-nitrobenzyl, methoxymethyl, acetoxymethyl or pivaloyloxymethyl ester.

9. The lithium salt of a compound of the formula (III):

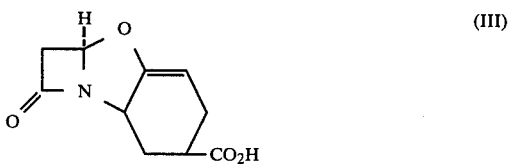

10. A method of effecting β-lactamase inhibition in mammals including humans in need thereof which comprises administering to such a mammal a β-lactamase inhibitory amount of a compound of the formula (II):

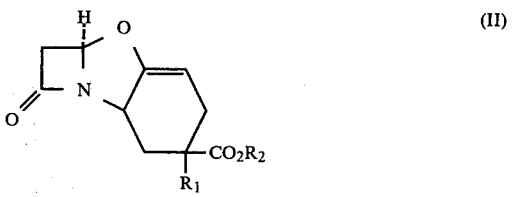

wherein R₁ is hydrogen or alkyl of 1 to 4 carbon atoms and CO₂R₂ is carboxyl or a pharmaceutically acceptable salt thereof, in combination with a pharmaceutically acceptable carrier.

11. A method according to claim 10 wherein the compound is sodium (5R)-Δ⁷,⁸-3-oxo-6-oxa-2-azatricyclo[5.4.0.0²,⁵]-undecene-10-carboxylate.

12. A method according to claim 10 wherein the compound is sodium (1S,5R,10S)-Δ⁷,⁸-3-oxo-6-oxa-2-azatricyclo-[5.4.0.0²,⁵]undecene-10-carboxylate.

13. A method according to claim 10 wherein the compound is (5R)-10-p-nitrobenzyloxycarbonyl-3-oxo-6-oxa-2-azatricyclo[5.4.0.0²,⁵]undec-7,8-ene.

14. The compound according to claim 1 which is (5R)-10-methoxycarbonyl-3-oxo-6-oxa-1-azatricyclo[5.4.0.0²,⁵]undec-7,8-ene.

15. The compound according to claim 1 which is (5R)-10-benzyloxycarbonyl-3-oxo-6-oxa-2-azabicyclo-[5.4.0.0²,⁵]-undec-7,8-ene.

16. The compound according to claim 1 which is sodium (1S,5R)-Δ⁷,⁸-3-oxo-6-oxa-2-azatricyclo-[5.4.0.0²,⁵undecene-10-carboxylate.

17. The compound according to claim 1 which is (5R)-10-methoxycarbonyl-10-methyl-3-oxo-6-oxa-2-azatricyclo [5.4.0.0²,⁵]undec-7,8-ene.

18. The compound which is (1S,5R,10S)-10-formyl-3-oxo-6-oxa-2-azatricyclo[5.4.0.0²,⁵]undec-7,8-ene.

19. The compound according to claim 1 which is sodium (1S,5R,10S)-7,8-3-oxo-6-oxa-2-azatricyclo-[5.4.0.0²,⁵]undecene-10-carboxylate.

20. The compound according to claim 1 which is (1S,5R,10S)-10-benzyloxycarbonyl-3-oxo-6-oxa-2-azatricyclo[5.4.0.0²,⁵]undec-7,8-ene.

21. The compound to claim 1 which is (1S,5R,10R)-10-benzyloxycarbonyl-3-oxo-6-oxa-2-azatricyclo[5.4.0.0²,⁵]undec-7,8-ene.

22. The compound according to claim 1 which is (5R)-10-pivaloyloxymethoxycarbonyl-3-oxo-6-oxa-2-azatricyclo[5.4.0.0²,⁵]undec-7,8-ene.

23. The compound according to claim 1 which is (5R)-10-p-nitrobenzyloxycarbonyl-3-oxo-6-oxa-2-azatricyclo[5.4.0.0²,⁵]undec-7,8-ene.

24. The compound according to claim 1 which is sodium (5R)-Δ⁷,⁸-3-oxo-6-oxa-2-azatricyclo[5.4.0.0²,⁵]-undecene-10-carboxylate.

25. The compound according to claim 1 which is sodium (1S,5R,10S)-Δ⁷,⁸-3-oxo-6-oxa-2-azatricyclo-[5.4.0.0²,⁵]undecene-10-carboxylate.

26. A pharmaceutical composition useful for effecting β-lactamase inhibition in mammals including humans which comprises a β-lactamase inhibitory amount of a compound of the formula (II):

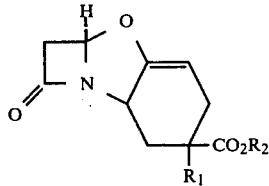

wherein R₁ is hydrogen or alkyl of 1 to 4 carbon atoms and CO₂R₂ is carboxyl or a pharmaceutically acceptable salt thereof, in combination with a pharmaceutically acceptable carrier.

27. A composition according to claim 26 wherein R₁ is hydrogen or methyl.

28. A composition according to claim 27 wherein the compound is of the formula (III):

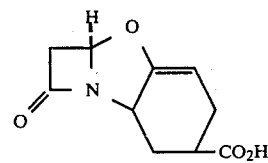

or a pharmaceutically acceptable salt thereof.

29. A composition according to claim 26 wherein the compound is in the form of an alkali or alkaline earth metal salt or ammonium salt.

30. A composition according to claim 29 wherein the salt is a lithium, sodium, potassium, calcium, magnesium or ammonium salt.

31. A pharmaceutical composition useful for effecting β-lactamase inhibition in mammals including humans which comprises a β-lactamase inhibitory amount of a compound of the formula (IV):

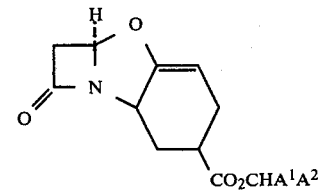

wherein A¹ is hydrogen, alkyl of 1 to 4 carbon atoms, alkenyl or alkynyl of 2 to 4 carbon atoms, phenyl, or phenyl substituted by alkyl of 1 to 4 carbon atoms, alkoxy of 1 to 4 carbon atoms, nitro or halogen; and A² is hydrogen, alkyl of 1 to 4 carbon atoms, alkoxy of 1 to 4 carbon atoms, alkanoyloxy of 1 to 5 carbon atoms, phenyl, or phenyl substituted by alkyl of 1 to 4 carbon atoms, alkoxy of 1 to 4 carbon atoms, nitro or halogen, in combination with a pharmaceutically acceptable carrier.

32. A pharmaceutical composition useful for effecting β-lactamase inhibition in mammals including humans which comprises a β-lactamase inhibitory amount of a compound of the formula (V):

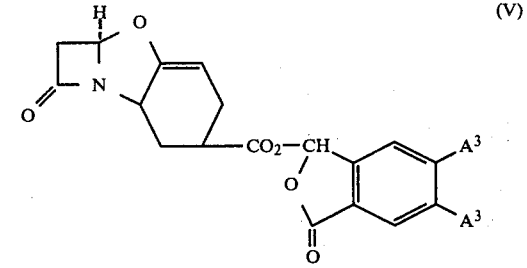

wherein A³ is hydrogen, methyl or methoxy, in combination with a pharmaceutically acceptable carrier.

33. A composition according to claim 31 wherein the compound is in the form of a methyl, ethyl, benzyl, p-methoxybenzyl, p-nitrobenzyl, methoxymethyl, acetoxymethyl or pivaloyloxymethyl ester.

34. A composition according to claim 26 wherein the compound is (5R)-10-methoxycarbonyl-3-oxo-6-oxo-1-azatricyclo[5.4.0.0²,⁵]undec-7,8-ene.

35. A composition according to claim 26 wherein the compound is (5R)-10-benzyloxycarbonyl-3-oxo-6-oxa-2-azatricyclo[5.4.0.0$^{2,5}$]-undec-7,8-ene.

36. A composition according to claim 26 wherein the compound is sodium (1S,5R)-$\Delta^{7,8}$-3-oxo-6-oxa-2-azatricyclo-[5.4.0.0$^{2,5}$]undecene-10-carboxylate.

37. A composition according to claim 26 wherein the compound is (5R)-10-methoxycarbonyl-10-methyl-3-oxo-6-oxa-2-azatricyclo[5.4.0.0$^{2,5}$]undec-7,8-ene.

38. A composition according to claim 26 wherein the compound is sodium (1S,5R,10S)-$\Delta^{7,8}$-3-oxo-6-oxa-2-azatricyclo-[5.4.0.0$^{2,5}$]undecene-10-carboxylate.

39. A composition according to claim 26 wherein the compound is sodium (1S,5R,10S)-$^{7,8}$-3-oxo-6-oxa-2-azatricyclo-[5.4.0.0$^{2,5}$]undecene-10-carboxylate.

40. A composition according to claim 26 wherein the compound is (1S,5R,10S)-10-benzyloxycarbonyl-3-oxo-6-oxa-2-azatricyclo[5.4.0.0$^{2,5}$]undec-7,8-ene.

41. A composition according to claim 26 wherein the compound is (1S,5R,10R)-10-benzyloxycarbonyl-3-oxo-6-oxa-2-azatricyclo[5.4.0.0$^{2,5}$]undec-7,8-ene.

42. A composition according to claim 26 wherein the compound is (5R)-10-pivaloyloxymethoxycarbonyl-3-oxo-6-oxa-2-azatricyclo[5.4.0.0$^{2,5}$]undec-7,8-ene.

43. A composition according to claim 26 in oral administration form.

44. A composition according to claim 26 in parenteral administration form.

45. A composition according to claim 26 wherein the compound is sodium (5R)-$\Delta^{7,8}$-3-oxo-6-oxa-2-azatricyclo[5.4.0.0$^{2,5}$]-undecene-10-carboxylate.

46. A method according to claim 10 wherein R$_1$ is hydrogen or methyl.

47. A method according to claim 46 wherein the compound is of the formula (III):

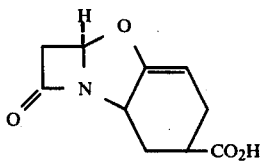

or a pharmaceutically acceptable salt thereof.

48. A method according to claim 10 wherein the compound is in the form of an alkali or alkaline earth metal salt or ammonium salt.

49. A method according to claim 48 wherein the salt is a sodium, potassium, calcium, magnesium or ammonium salt.

50. A method of effecting β-lactamase inhibition in mammals including humans in need thereof which comprises administering to such a mammal a β-lactamase inhibitory amount of a compound of the formula

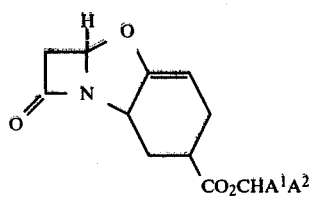

wherein A$^1$ is hydrogen, alkyl of 1 to 4 carbon atoms, alkenyl or alkynyl of 2 to 4 carbon atoms, phenyl, or phenyl substituted by alkyl of 1 to 4 carbon atoms, alkoxy of 1 to 4 carbon atoms, nitro or halogen; and A$^2$ is hydrogen, alkyl of 1 to 4 carbon atoms, alkoxy of 1 to 4 carbon atoms, alkanoyloxy of 1 to 5 carbon atoms, phenyl, or phenyl substituted by alkyl of 1 to 4 carbon atoms, alkoxy of 1 to 4 carbon atoms, nitro or halogen, in combination with a pharmaceutically acceptable carrier.

51. A method of effecting β-lactamase inhibition in mammals including humans in need thereof which comprises administering to such a mammal a β-lactamase inhibitory amount of a compound of the formula

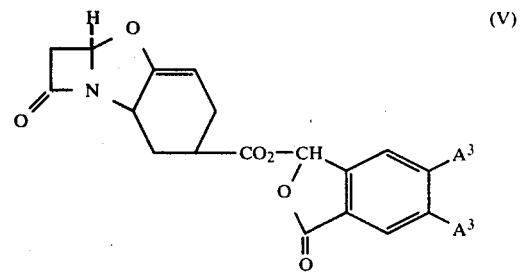

wherein A$^3$ is hydrogen, methyl or methoxy, in combination with a pharmaceutically acceptable carrier.

52. A method according to claim 50 wherein the compound is in the form of a methyl, ethyl, benzyl, p-methoxybenzyl, p-nitrobenzyl, methoxymethyl, acetoxymethyl or pivaloyloxymethyl ester.

53. A method according to claim 10 wherein the compound is (5R)-10-methoxycarbonyl-3-oxo-6-oxa-1-azatricyclo[5.4.0.0$^{2,5}$]undec-7,8-ene.

54. A method according to claim 10 wherein the compound is (5R)-10-benzyloxycarbonyl-3-oxo-6-oxa-2-azabicyclo[5.4.0.0$^{2,5}$]undec-7,8-ene.

55. A method according to claim 10 wherein the compound is sodium (1S,5R)-$\Delta^{7,8}$-3-oxo-6-oxa-2-azatricyclo-[5.4.0.0$^{2,5}$]undecene-10-carboxylate.

56. A method according to claim 10 wherein the compound is (5R)-10-methoxycarbonyl-10-methyl-3-oxo-6-oxa-2-azatricyclo[5.4.0.0$^{2,5}$]undec-7,8-ene.

57. A composition according to claim 26 wherein the compound is (5R)-10-p-nitrobenzyloxycarbonyl-3-oxo-6-oxa-2-azatricyclo[5.4.0.0$^{2,5}$]undec-7,8-ene.

58. A method according to claim 10 wherein the compound is sodium (1S,5R,10S)-$^{7,8}$-3-oxo-6-oxa-2-azatricyclo-[5.4.0.0$^{2,5}$]undecene-10-carboxylate.

59. A method according to claim 10 wherein the compound is (1S,5R,10S)-10-benzyloxycarbonyl-3-oxo-6-oxa-2-azatricyclo[5.4.0.0$^{2,5}$]undec-7,8-ene.

60. A method according to claim 10 wherein the compound is (1S,5R,10R)-10-benzyloxycarbonyl-3-oxo-6-oxa-2-azatricyclo[5.4.0.0$^{2,5}$]undec-7,8-ene.

61. A method according to claim 10 wherein the compound is (5R)-10-pivaloyloxymethoxycarbonyl-3-oxo-6-oxa-2-azatricyclo[5.4.0.0$^{2,5}$]undec-7,8-ene.

62. A method according to claim 10 wherein the administration is oral.

63. A method according to claim 10 wherein the administration is parenteral.

64. A composition according to claim 32 wherein the compound is in the form of the phthalidyl ester.

65. A method according to claim 51 wherein the compound is in the form of the phthalidyl ester.

66. A compound according to claim 7 wherein the compound is in the form of the phthalidyl ester.

* * * * *